United States Patent [19]

Suginaka et al.

[11] 4,407,941
[45] Oct. 4, 1983

[54] PHOTOGRAPHIC ELEMENT WITH PYRAZOLE ELECTRON DONORS

[75] Inventors: Shunji Suginaka; Ryuichiro Kobayashi; Satoru Ikeuchi; Noboru Mizukura; Noriko Fujita, all of Hino, Japan

[73] Assignee: Konishiroku Photo Industry Co., Ltd., Tokyo, Japan

[21] Appl. No.: 355,464

[22] Filed: Mar. 8, 1982

[30] Foreign Application Priority Data

Mar. 13, 1981 [JP] Japan .................................. 56-36162

[51] Int. Cl.³ .......................... G03C 1/40; G03C 5/30; G03C 5/54
[52] U.S. Cl. .................................. 430/566; 430/218; 430/440; 430/443; 430/483; 430/959
[58] Field of Search ............... 430/218, 223, 443, 440, 430/483, 959, 566

[56] References Cited

U.S. PATENT DOCUMENTS 4,139,379  2/1979  Chasman et al. .................... 430/223
4,266,002  5/1981  McCreary et al. .................. 430/218
4,310,612  1/1982  Mooberry et al. ................... 430/223

Primary Examiner—Richard L. Schilling
Attorney, Agent, or Firm—Jordan B. Bierman; Linda Bierman

[57] ABSTRACT

A photographic element comprising a support provided thereon with at least one light-sensitive silver halide emulsion layer containing a nondiffusible compound which receives at least one electron in an alkaline condition to release a photographically useful material and a nondiffusible electron donor or a precursor thereof having the following formula (I) or (II):

Formula (I)         Formula (II)

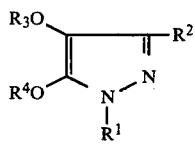 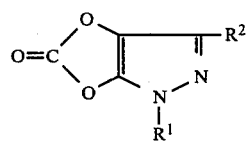

wherein $R^1$ represents hydrogen, an alkyl, an aryl or a heterocyclic group, $R^2$ represents hydrogen, an alkyl, an aryl, a heterocyclic, an amino, a carbamide, a sulfonamide, a sulfamoyl, a carbamoyl or a ureido group, $R^3$ and $R^4$ each is hydrogen, $-COR^5$, $-SO_2R^6$ or $-CSR^7$ wherein $R^5$ and $R^6$ each is a substituted or unsubstituted, respectively, alkyl, alkenyl, aryl, heterocyclic, alkylamino, alkyloxy, aryloxy, alkylthio, arylthio, alkyloxycarbonyl or aryloxycarbonyl group, and $R^7$ is a substituted or unsubstituted alkylamino or arylamino group, said $R^4$ being allowed to form a ring together with said $R^1$.

1 Claim, No Drawings

PHOTOGRAPHIC ELEMENT WITH PYRAZOLE ELECTRON DONORS

The present invention relates to a novel photographic element, and more particularly to a photographic element which contains a nondiffusible compound capable of releasing a diffusible photographically useful material and a nondiffusible electron donor or a precursor thereof.

It is in generally known in the art that in the photographic image forming technology, an image dye-providing compound used in the insoluble form is changed imagewise so as to become more soluble form to thereby provide an imagewise distribution of dye diffusible. For example, the use of a ballast-stabilized compound which is subjected to a reduction reaction to release a diffusible component is disclosed in U.S. Pat. No. 4,139,379. This method is called the "BEND" method, wherein a reducing agent is made present as the reversed function of the silver halide development by an auxiliary agent of a silver halide developer, and on the reaction of the reducing agent with the foregoing ballast-stabilized compound a diffusible component is released.

And as the reducing agent which is capable of reducing the above ballast-stabilized compound, i.e., the electron donor or a precursor thereof, benz-iso-oxazolones, β-diketones, saccharins, lactones, protohydroquinones, ascorbic acids, aminophenols, aminonaphthols, hydroquinones, and the like, are disclosed. Further, other β-diketone-type compounds are described in Research Disclosure No. 19429, and saccharins in Research Disclosure No. 19507. These preferred electron donors are those of which half-life period in the redox reaction rate under the processing condition of the photographic element is up to 30 minutes.

When a silver halide developing agent is used as an electron donor, as a result of the development of a silver halide, the electron donor is oxidized and can no longer acts as electron donor, while the electron donor remaining in the area which has not been developed reduces the material to be reduced, thus resulting in the release of a photographic material.

Preferred electron donors in this case are those of which half-life period of the electron donor in the redox reaction with the exposed silver halide is as short as one fifth to one tenth of that of the electron donor in the redox reaction thereof with the material to be reduced.

Typical electron donor which are also silver halide developing agents include, hydroxylamines such as ascorbic acid, diethyl hydroxylamino, trihydroxypyrimidines such as 2-methyl-4,5,6-trihydroxypyrimidine, and the like. Those electron donors which have a weak or no silver halide developability may also be used as precursors which are to provide electron donor by hydrolysis. Such precursors include, e.g., lactones, hydroquinones whose at least one hydroxy group is protected with a hydrolyzable group, and iso-oxazolones.

An electron donor which is weak somehow or other in the silver halide developability may preferably be incorporated as a nondiffusible precursor in combination with the material to be reduced into a photographic element. The oxide of the silver halide developing agent produced as a result of development of silver halide reacts with the electron donor produced by hydrolysis to oxidize the electron donor, and the residual electron donor reduces the material to be reduced, thus resulting in the release of a photographically useful material.

The silver halide developing agent used herein is desired to be such that the half life period of the electron donor in the redox reaction thereof with the material to be reduced is from 5 to 10 times as long as that in the redox reaction between the material to be reduced and the electron donor.

As has been described above, electron donors are essential to the photographic image forming method of the type of releasing diffusible photographically useful components. However, the above-described electron donors which have been known to date are compounds relatively weak in the reduction action thereof, so that as for the above-described materials to be reduced which are subjected to reduction action to release photographically useful components there have necessarily been used such unstable compounds as capable of releasing photographically useful components in weak reduction actions. Accordingly, it has been considered difficult, when incorporated into a silver halide emulsion layer, to find materials to be reduced which are excellent in the stability in storage.

SUMMARY OF THE INVENTION

It is an object of the present invention to provide a photographic element containing an electron donor or a precursor thereof which is suitable for obtaining a light-sensitive material which, when used in combination with a nondiffusible compound capable of releasing a diffusible photographically useful material, has a high image forming efficiency and is excellent in the stability in storage.

Thus the present invention more specifically relates to a photographic element characterized by having on the support thereof at least one light-sensitive silver halide emulsion layer containing a nondiffusible compound which, on receiving at least one electron in an alkaline condition, is capable of releasing a photographically useful substance, and a nondiffusible electron donor or a precursor thereof having the following formula (I) or (II):

Formula (I) 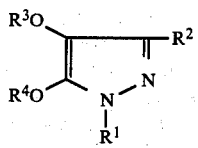  Formula (II) 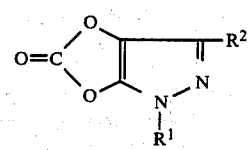

wherein $R^1$ represents hydrogen, or an alkyl, an aryl or a heterocyclic group (each of afore-mentioned group may be substituted), $R^2$ represents hydrogen, or an alkyl, an aryl, a heterocyclic, an amino, a carbamide, a sulfonamide, a sulfamoyl, a carbamoyl, or a ureido group (each of afore-mentioned group may be substituted), $R^3$ and $R^4$ independently represent hydrogen, or a $—COR^5$, a $—SO_2R^6$, or a $—CSR^7$ group wherein $R^5$ and $R^6$ independently represent an alkyl, an alkenyl, an aryl, a heterocyclic, an alkylamino, an arylamino, an alkyloxy, an aryloxy, an alkylthio, an arylthio, an alkyloxycarbonyl, or an aryloxycarbonyl group (each of afore-mentioned group may be substituted), and $R^7$ represents an alkylamino or an arylamino group (each group may be substituted), said $R^4$ being allowed to form a ring together with said $R^1$.

DETAILED DESCRIPTION OF THE INVENTION

The present invention is described in further detail below:

Alkyl group represented by $R^1$ is preferably selected from one having from 1 to 22 carbon atoms; more specifically, a halogen-substituted alkyl, a hydroxy-substituted alkyl, a phenyl-substituted alkyl, and the like, are preferred. As the aryl group, a substituted or unsubstituted phenyl group is preferable. More specifically, unsubstituted phenyl group, a halogen-substituted phenyl, a halogen-alkyl-substituted phenyl, a halogen-alkoxy-substituted phenyl, or other substituted phenyl with an ester, an acylamide, an alkoxy may be used more preferably. Further, as the heterocyclic group, a benzothiazolyl group, a benzoxazolyl group, a benzimidazolyl group, a picolysinyl group or a piperidinyl group is preferred; particularly among them, benzothiazolyl, benzoxazolyl and benzimidazolyl groups are preferred.

As the alkyl, aryl, and heterocyclic group defined as $R^2$, the same group defined as to $R^1$ can be mentioned. As the amino group, amino group, an alkyl-substituted amino group, and an aryl-substituted amino group are preferred. As the preferable carbamide group, a substituted or unsubstituted alkylcarbamide group or arylcarbamide group can be mentioned. As the preferable sulfonamide group, a substituted or unsubstituted alkylsulfonamide or arylsulfonamide groups can be mentioned. As the preferable sulfamoyl group, a substituted or unsubstituted alkylsulfamoyl or arylsulfamoyl group can be mentioned. As the preferable carbamoyl group, a substituted or unsubstituted alkylcarbamoyl or arylcarbamoyl group can be mentioned. And as the preferable ureido group, a substituted or unsubstituted alkylureido and arylureido group can be mentioned.

As the alkyl group represented by $R^5$ or $R^6$ in Formula (I), a substituted or unsubstituted alkyl group having from 1 to 22 carbon atoms such as, methyl, ethyl, t-butyl, octyl, 2-chlorobutyl, 2-phenyl-propyl, and the like are preferable. Similarly, as the alkenyl group a substituted or unsubstituted alkenyl group having from 2 to 22 carbon atoms, such as vinyl, isopropenyl, allyl or styryl group; as the aryl group a substituted or unsubstituted aryl group having from 6 to 25 carbon atoms such as, phenyl, naphthyl, 2,4,6-trichlorophenyl and 2,4-dimethyl-6-chlorophenyl group; as the heterocyclic group a substituted or unsubstituted, benzothiazolyl, benzoxazolyl, benzimidazolyl or pyrrolidinyl group; as the alkylamino group a substituted or unsubstituted alkylamino group having from 1 to 22 carbon atoms such as, methylamino, ethylamino, t-butylamino or phenyl-ethylamino group; as the arylamino group a substituted or unsubstituted arylamino group having from 6 to 25 carbon atoms such as anilino, 4-chloroanilino or 4-aminoanilino; as the alkoxy group a substituted or unsubstituted alkoxy group having from 1 to 22 carbon atoms such as ethoxy, isopropyloxy, β-phenylethoxy; as the aryloxy group a substituted or unsubstituted aryloxy group having from 6 to 25 carbon atoms such as phenoxy, naphthyloxy, 4-methoxycarbonylphenoxy group; as the alkylthio group a substituted or unsubstituted alkylthio group having from 1 to 22 carbon atoms such as ethylthio, benzylthio or n-dodecylthio group; as the arylthio group a substituted or unsubstituted arylthio group having from 6 to 25 carbon atoms such as phenylthio or naphthylthio group; as the alkoxycarbonyl group a substituted or unsubstituted alkoxycarbonyl group having from 1 to 22 carbon atoms such as ethoxycarbonyl, n-octyloxycarbonyl or β-phenylethoxycarbonyl group; and as the aryloxycarbonyl group a substituted or unsubstituted aryloxycarbonyl groups having from 6 to 25 carbon atoms such as phenoxycarbonyl, naphthyloxycarbonyl or 4-chlorophenoxycarbonyl groups can be mentioned.

And as the preferable substituted or unsubstituted alkylamino and arylamino groups represented by the $R^7$, the same as those groups as defined in $R^5$ and $R^6$ can be mentioned. The $R^4$ may be allowed to form a ring together with the $R^1$, and in this case preferable ring is a lactone ring or a sultone ring.

The nondiffusible electron donor of the present invention is provided with nondiffusibility by increasing the molecular weight thereof, utilizing one or some of the above-mentioned substituents.

The following are typical examples of groups represented by the $R^3O-$ and $R^4O-$ in Formula (I), but the present invention is not limited thereto.

EXAMPLES (1) —OH (2) —OCOCH₃

(3) —OCOC₂H₅

(4) —OCOC₃H₇(n)

(5) —OCOC₃H₇(iso)

(6) —OCOC₄H₉(n)

(7) —OCOC₄H₉(iso)

(8) —OCOC₄H₉(t)

(9) —OCOCH₂Cl

(10) —OCOCH=CH— 

(11) —OCO—CH₂— 

(12) —OCO— 

(13) —O—SO₂CH₃

(14) —O—SO₂C₂H₅

(15) —O—SO₂C₁₂H₂₅

(16) —O—SO₂— 

(17) —O—SO₂— 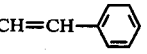—CH₃

(18) —OCONHCH₃

(19) —OCONHC(CH₃)₃

(20) —OCONH— 

(21) —OSO₂NHCH₃

(22) —OSO₂NHCH₃

(23) —OSO₂NH— 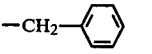

(24) —OCOOCH₂— 

(25) —OCOS— 

(26) $-OC(=S)-N(CH_3)_2$

(27) —OCCOO—  (with C=O)

Examples of electron donors applicable to the present invention are illustrated below, but the present invention is not limited thereto:

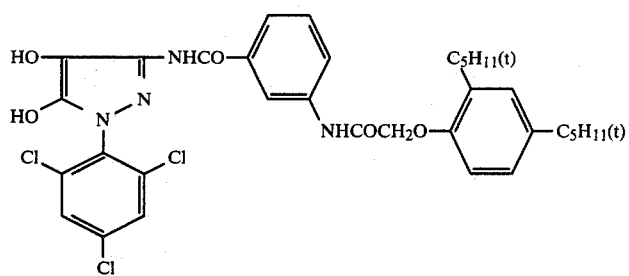
(1)
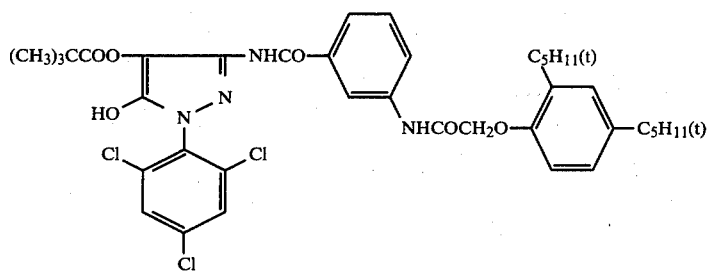
(2)
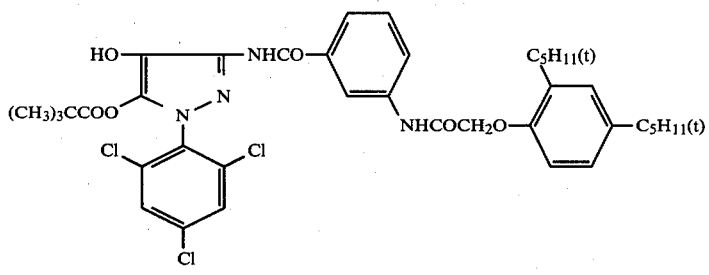
(3)
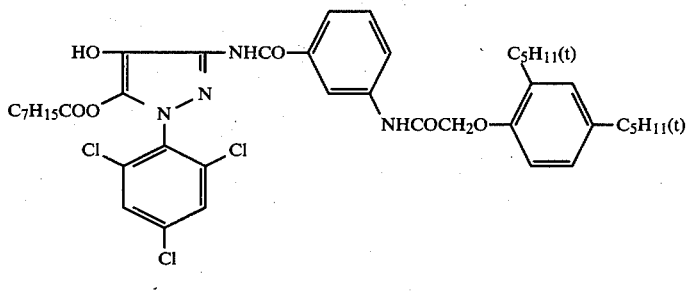
(4)
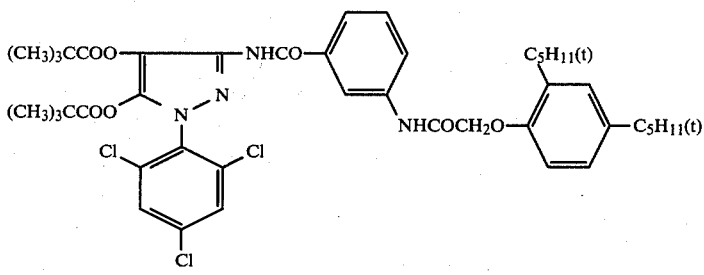
(5)

-continued
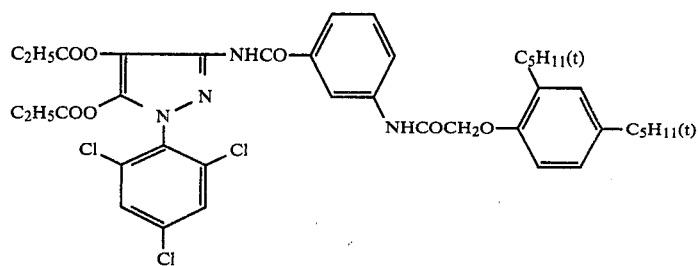 (6)
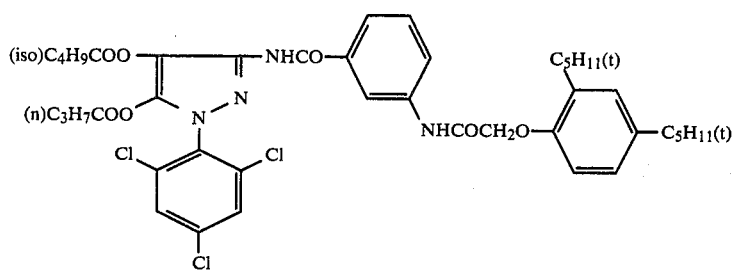 (7)
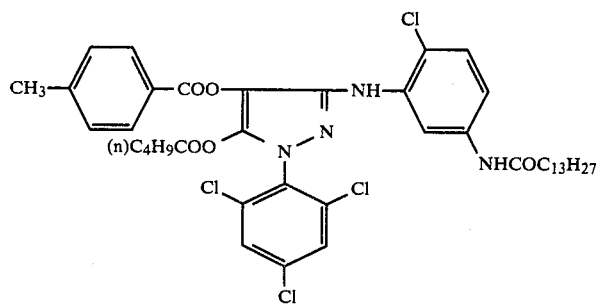 (8)
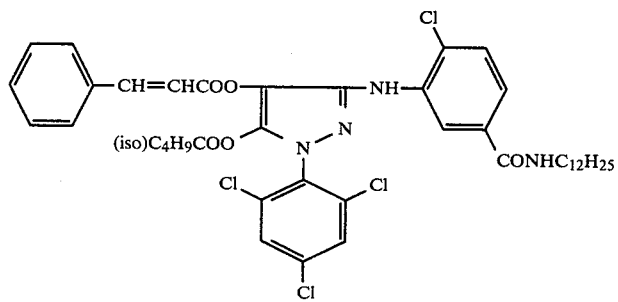 (9)
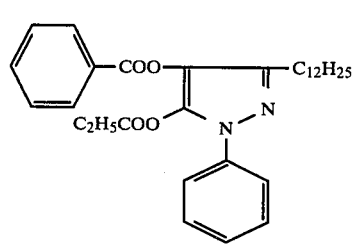 (10)
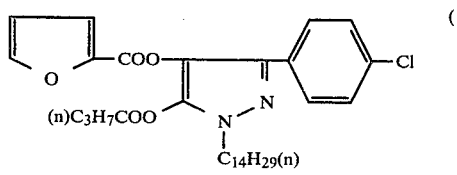 (11)
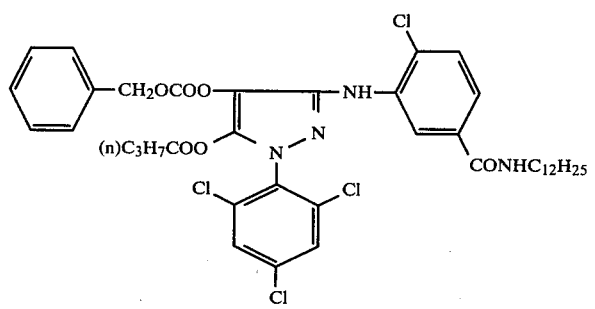 (12)

-continued
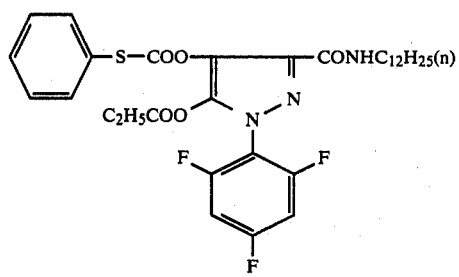 (13)
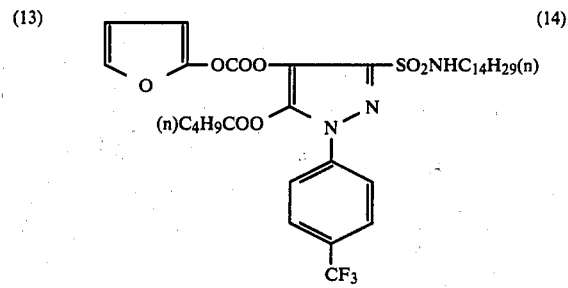 (14)
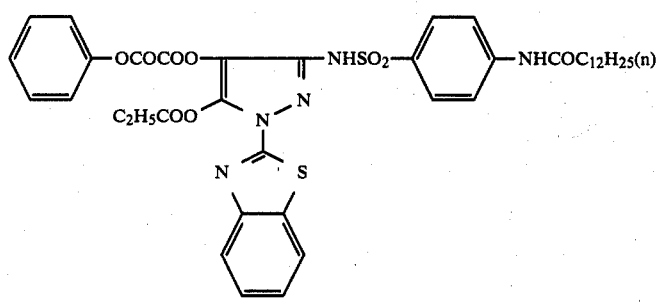 (15)
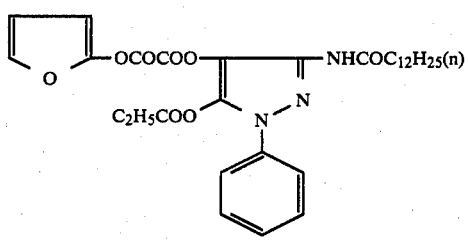 (16)
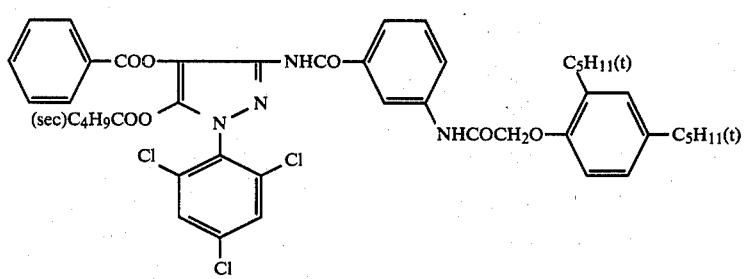 (17)
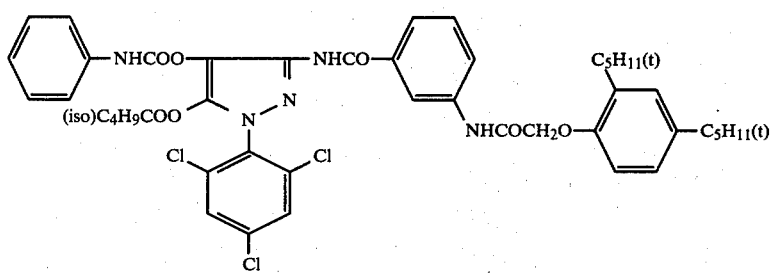 (18)

-continued
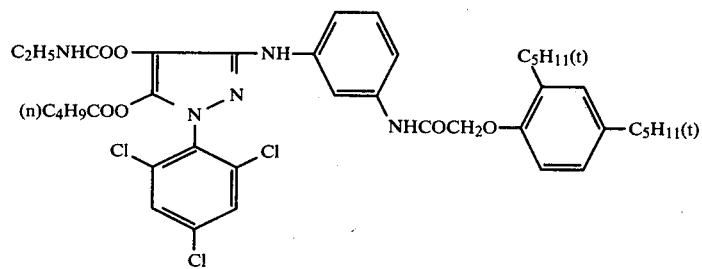 (19)
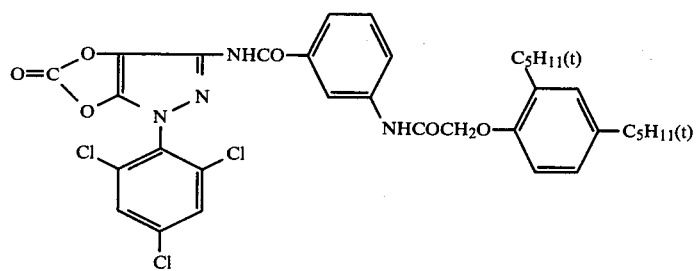 (20)
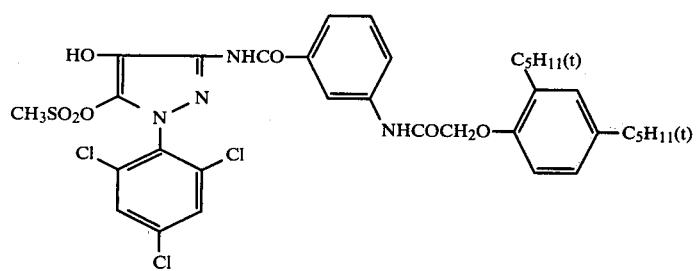 (21)
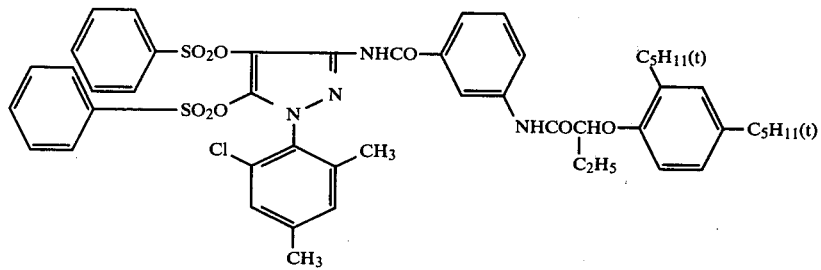 (22)
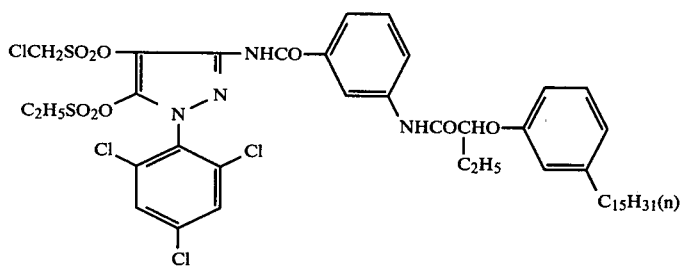 (23)

-continued
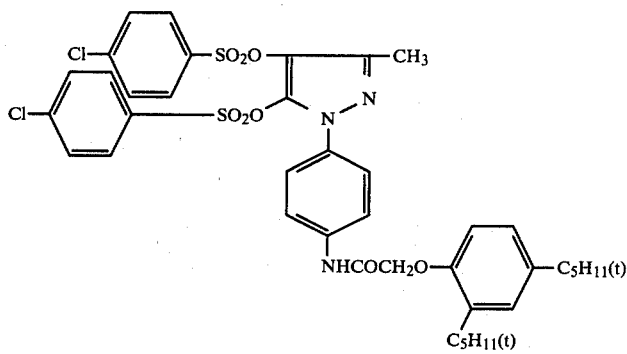
(24)
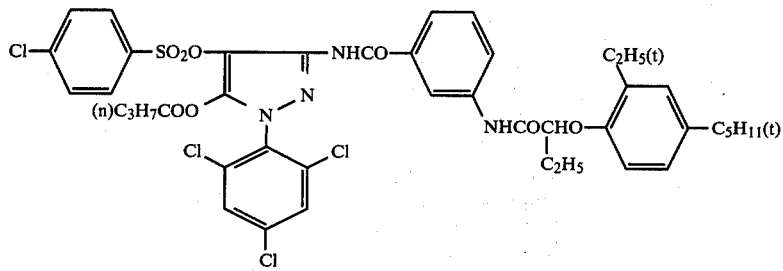
(25)
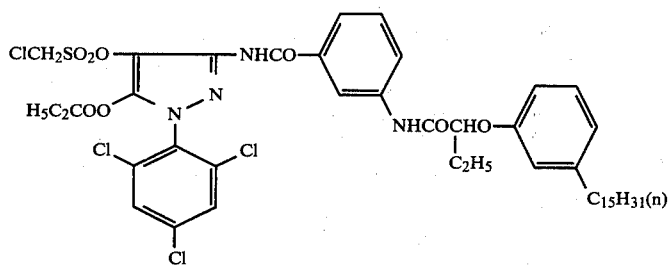
(26)
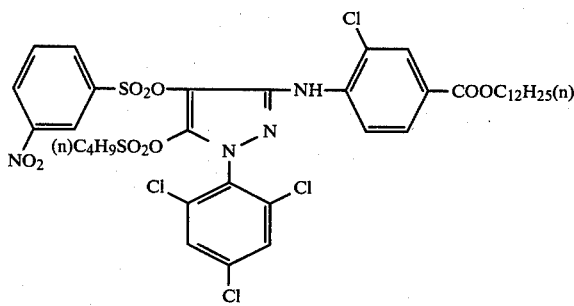
(27)
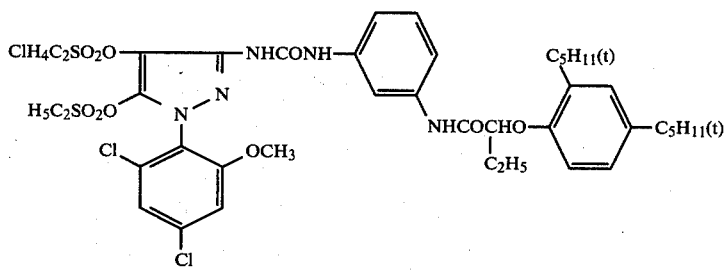
(28)
Examples of the synthesis of pyrazole compounds, the electron donors of the present invention, are illustrated below:
SYNTHESIS EXAMPLE 1
Synthesis of Exemplified Compound (3)
4 grams of 1-(2,4,6-trichlorophenyl)-3-[3-(2,4-di-t-amylphenoxyacetamide)benzamide]-4-hydroxy-5- pyrazolone are dissolved into 50 ml of ethyl acetate, and to the solution is added 0.7 g of pivaloyl chloride and further added slowly 0.5 g of pyridine with stirring at room temperature. After about 30 minutes of the reaction, 50 ml of water are added to the reactant to sufficiently wash the ethyl acetate layer. The organic substance layer is then separated to be dried, concentrated under reduced pressure, and recrystallized in a mixed solvent of n-hexane with ethyl acetate, whereby a colorless powdery product is obtained. Yield: 35 g, M.P. 177° to 178° C.

SYNTHESIS EXAMPLE 2

Synthesis of Exemplified Compound (4)

10 grams of 1-(2,4,6-trichlorophenyl)-3-[3-(2,4-di-t-amylphenoxyacetamide)benzamide]-4-hydroxy-5-pyrazolone are dissolved into 100 ml of ethyl acetate, and to the solution are added 1.5 g of pyridine, and further added slowly 2.5 g of octanoyl chloride at room temperature. After three hours of the reaction, water is added to the reactant for the washing thereof. The solvent is removed to concentrate the reactant under reduce pressure. The reactant is then recrystallized in petroleum ether, whereby a colorless powdery product is obtained. Yield: 9.5 g, M.P. 110° to 112° C.

SYNTHESIS EXAMPLE 3

Synthesis of Exemplified compound (21)

10 grams of 1-(2,4,6-trichlorophenyl)-3-{3-[α-2,4-di-t-amylphenoxyacetamide]benzamide}-4-hydroxy-5-pyrazolone are dissolved into a mixed solvent of 100 ml of ethyl acetate with 100 ml of acetonitrile, and to the solution are added 1.5 g of pyridine, and further added 2 g of methane-sulfonic acid chloride, spending one hour at room temperature. After 20 hours of the reaction, the reactant is poured into 500 ml of iced water, to which is then added 400 ml of ethyl acetate to extract the objective product. The solvent is removed under reduced pressure, and the residuum is then recrystallized in a mixed solvent of ethyl acetate with n-hexane, thereby obtaining a light yellow needle crystals. Yield: 9 g, 80%, M.P. 129° to 130° C. Mass spectrometry in accordance with the electrolytic elimination method: $M^+$ 764.

The above-described electron donor of the present invention have relatively strong reduction power; for example, as the value obtained by the measurement made in a 0.1 N aqueous NaOH solution, with respect to a saturated calomel electrode, a known ascorbic acid electron donor shows approximately −250 m.v., while benzoxazolone electron donor shows approximately −400 m.v., and the foregoing electron donors of the present invention are more negative than these known electron donors and these donors preferably have at least the potential of not more than −400 m.v.

Accordingly, in the present invention, if a compound is of the so-called BEND type whose potential comes into between the above-mentioned potential owned by the electron donor of the present invention and the potential owned by the developing agent used for the reduction of a silver halide, the compound may be reduced by the electron donor of the present invention in an alkaline condition to thereby release a photographically useful substance or group. The term "photographically useful substance or group" used herein means a compound which plays a photographically effective roll in the photographic layer concerned, typical examples of which are, e.g., development inhibitors and dyes, and in addition, development accelerators, hardeners, and the like, may also be included therein.

Nondiffusible compounds which are usable in combination with the electron donor of the present invention and which receive at least one electron in an alkaline condition to release a photographically useful substance or group include those compounds used in the quinonemethide method, BEND method, and CLER method.

The previously mentioned U.S. Pat. No. 4,139,379 describes the BEND method which uses BEND compounds, examples of which compounds include:

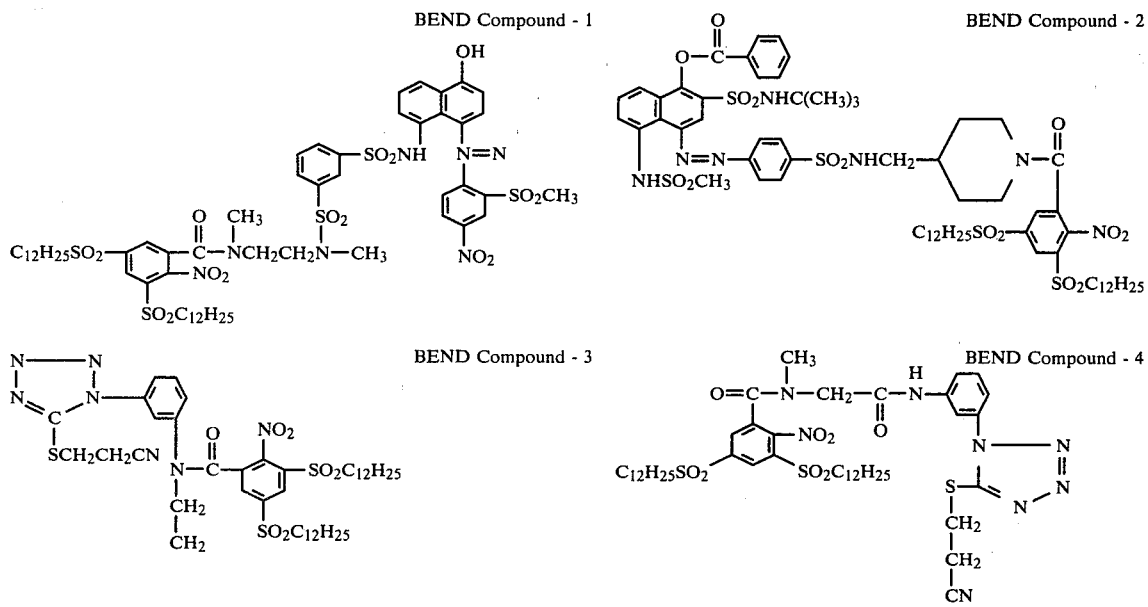

And the quinonemethide method is described in Japanese Patent Publication Open to Public Inspection (hereinafter referred to as Japanese Patent O.P.I. Publication) No. 130,927/1979.

Further, in the CLER method, metallic complex compounds whose ligand exchange becomes active by reduction, such as those having the formula (III), may also be used in combination with electron donors. The CLER method is described in detail in Japanese Patent Application No. 183,573/1980, now Japanese patent O.P.I. No. 105738/1982.

Formula (III)

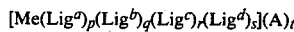

Wherein Me represents a transition metal such as, e.g., nickel, cobalt; $Lig^a$ and $Lig^b$ each is a multidentate ligand; $Lig^c$ and $Lig^d$ each is a coordinatable ligand; A is a counter ion; p is an integer of from 1 to 3, q is an integer of from zero to 2 (provided that when q is zero, p is an integer of not less than 2); r and s each is an integer of from zero to 4; and t is an integer of from zero to 6.

duces a photographically useful substance. This mechanism is not clearly known, but it is assumed that the center metal of the complex is reduced by the electron-transfer reaction and the complex is changed from being inert in the ligand exchange to being active in the ligand exchange, whereby the ligand exchange reaction between the ligand containing the residue of a photographically useful material and other ligand (e.g., aquo molecule) becomes accelerated, and therefore the bonding between the metal and the ligand containing the photographically useful material is severed and the diffusible photographically useful material is rapidly released.

Such metallic complex compounds having Formula (III) are called the CLER compound, examples of which are enumerated below (see Japanese Patent Application No. 183,573/1980) now Japanese patent O.P.I. No. 105,738/1982:

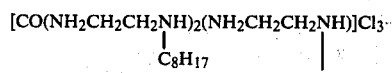
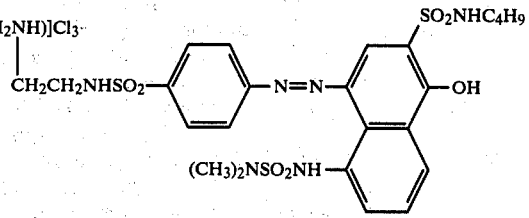

CLER Compound - 1

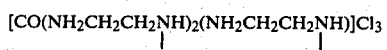
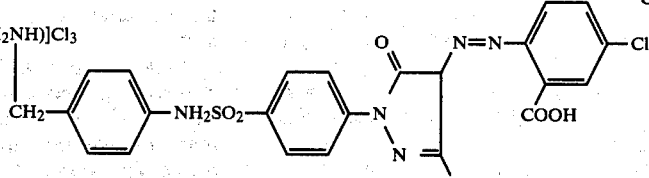

CLER Compound - 2

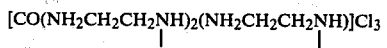
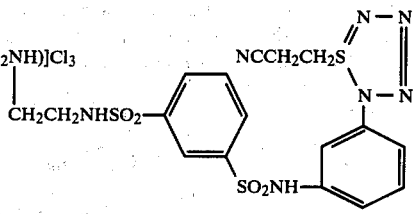

CLER Compound - 3

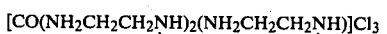
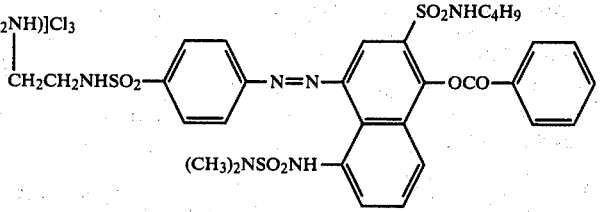

CLER Compound - 4

A metallic complex having Formula (III) is a nondiffusible, ligand-exchange-inert complex which is such that it coordinates at least one multidentate ligand, and at least one of the multidentate ligands has a residue of a diffusible photographically useful material, and the complex, when reduced in an alkaline condition, becomes active in the ligand exchange to release the photographically useful substance or group; that is, the complex nondiffusible in an alkaline condition, when subjected to the reduction in an alkaline condition, pro- As for the amount of the above-mentioned electron donor to be used in the present invention, the proportion of the nondiffusible compound capable of releasing a photographically useful substance or group to the electron donor is preferably within the range in terms of parts by weight of from 4:1 to 1:6, and more preferably from 2:1 to 1:2.

The amount of the electron donor to be used with respect to the silver halide, although differing according to the kind of the silver halide used or the kind of the material to be reduced, is generally in the quantity of $1\times10^{-3}$ to 0.5 mol, preferably $1\times10^{-2}$ to $2\times10^{-1}$ mol per mol of the silver halide.

The photographic element of the present invention is characterized by the composition thereof having on the support thereof at least one light-sensitive silver halide layer containing a nondiffusible compound capable of releasing a photographically useful substance or group by the reduction in an alkaline condition in combination with the electron donor. Silver halides applicable to the above light-sensitive silver halide emulsion layer include arbitrary silver halides for use in normal silver halide photographic light-sensitive materials such as silver chloride, silver bromide, silver iodide, silver chlorobromide, silver iodobromide, silver chloroiodobromide, and the like.

The foregoing silver halide emulsion may be sensitized by known chemical sensitizers. Such chemical sensitizers include, e.g., noble metal sensitizers, sulfur sensitizers, selenium sensitizers and reduction sensitizers, and these sensitizers may be used singly or in combination.

As the binder for use in the composition of the above silver halide emulsion layer, there may be used hydrophilic colloids such as natural or synthetic hydrophilic macromolecular compounds, and the most preferred one among them is gelatin.

The support employable in the photographic element of the present invention includes any one of conventionally known support, e.g., baryta paper, polyethylene-coated paper, polypropylene synthetic paper, glass plates, cellulose acetate, cellulose nitrate, polyester film such as, polyethylene terephthalate, and the like, polyamide film, polypropylene film, polycarbonate film, polystyrene film, and the like.

The photographic element of the present invention is useful for black-and-white, color (including so-called false color) photographic materials, and may be applied to silver halide photographic light-sensitive materials for various purposes such as black-and-white films for general use, black-and-white films for photolithography, X-ray films, electron-sensitive films, high-resolution black-and-white films, color films for general use, color X-ray films, diffusion-transfer-type color films, and the like.

In the above-mentioned various uses, one of the photographic light-sensitive materials to which the photographic element of the present invention is mot preferably applicable is the color diffusion transfer photographic light-sensitive material. In the light-sensitive material, in addition to the light-sensitive silver halide emulsion layer of the present invention on the known material support thereof, the support may be provided thereon at need with various composition components such as a protective layer, filter layer, subbing layer, light-reflective layer, opaque layer, acid neutralizing layer, image-receiving layer, and the like.

The photographic element of the present invention, after being image-wise exposed, is processed in a processing solution containing a reducing agent.

As the reducing agent of the processing solution used in the present invention, a developing agent is advantageously used. Developing agents usable herein include, for example, hydroquinone, 2,5-dichlorohydroquinone, and 2-chlorohydroquinone; aminophenol compounds such as 4-aminophenol, N-methyl aminophenol, 3-methyl-4-aminophenol, 3,5-dibromoaminophenol, etc.; catechol compounds such as catechol, 4-cyclohexyl catechol, 3-methoxycatechol, 4-(N-octadecylamino) catechol, etc.; and phenylenediamine compounds such as N,N-diethyl-p-phenylenediamine, 3-methyl-N,N-diethyl-p-phenylenediamine, 3-methoxy-N-ethyl-N-ethoxy-p-phenylenediamine, N,N,N',N'-tetramethyl-p-phenylenediamine, etc. Particularly preferred examples are 3-pyrazolidone compounds, for example, 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis-(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(3-chlorophenyl)-3-pyrazolidone, 1-(4-chlorophenyl)-3-pyrazolidone, 1-(4-tolyl)-4-methyl-3-pyrazolidone, 1-(2-tolyl)-4-methyl-3-pyrazolidone, 1-(4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, and 5-methyl-pyrazolidone.

Such combination of the developing agents as disclosed in U.S. Pat. No. 3,039,869 may also be used. Such developing agents may be used in a processing composition, or alternatively at least part of the agents may also be incorporated in an arbitrary layer or a plurality of layers of the photographic element, e.g., in the silver halide emulsion layer, dye image forming material-containing layer, interlayer and in the image-receiving layer.

As has been described in detail above, the electron donors of the present invention having Formula (I) or Formula (II), since they have stronger reduction power than conventional ones, permit the wider selection of the combination of nondiffusible compounds capable of forming diffusible photographically useful materials by the reduction in an alkaline condition, and therefore enable to avoid the use of such unstable compounds as to release the foregoing photographically useful material with the weak reduction power thereof, so that they are not only useful for obtaining a stable light-sensitive material but improve the image forming efficiency, and thus they may be advantageously used also for the silver-saving measure.

The photographic element of the present invention is illustrated in further detail with reference to examples below:

EXAMPLE 1

A multicolor image transfer type photographic element was prepared by coating on a 150 μm-thick transparent poly(ethylene terephthalate) film support in order from the support side the following layers:

(1) an image-receiving layer having 2.7 g/m² of gelatin and 2.7 g/m² of poly(styrene-co-N-benzyl-N,N-dimethyl-N-methacryloyl-aminophenyl-methyl ammonium chloride-co-divinyl benzene) (molar ratio: 48:48:4);

(2) a white light-reflective layer having 2.2 g/m² of gelatin and 22 g/m² of titanium dioxide;

(3) an opaque layer having 1.8 g/m² of gelatin and 2.8 g/m² of carbon black;

(4) a red-sensitive, cyan dye-providing layer having 1.08 g Ag/m² of a red-sensitive silver iodobromide emulsion, 0.47 g/m² of the following cyan BEND compound (A), 0.50 g/m² of Exemplified pyrazole electron donor (3), 0.97 g/m² of N,N-diethyl-laurylamide, and 1.94 g/m² of gelatin;

(5) an interlayer having 0.45 g/m² of 2-acetyl-5-sec-octadecyl hydroquinone, 0.225 g/m² of dibutyl phthalate, and 1.35 g/m² of gelatin, and a magenta filter dye;

(6) a green-sensitive, magenta dye-providing layer having 1.62 g Ag/m² of a green-sensitive silver iodobromide emulsion, 0.67 g/m² of the following magenta BEND compound (B), 0.96 g/m² of Exemplified pyrazole electron donor (3), 1.63 g/m² of N,N-diethyl-laurylamide, and 3.26 g/m² of gelatin;

(7) an interlayer having 0.45 g/m² of 2-acetyl-5-sec-octadecyl hydroquinone, 0.225 g/m² of dibutyl phthalate, 1.35 g/m² of gelatin, and a yellow filter dye;

(8) a blue-sensitive, yellow dye-providing layer having 1.62 g Ag/m² of a blue-sensitive silver iodobromide emulsion, 0.58 g/m² of the following yellow BEND compound (C), 1.04 g/m² of Exemplified pyrazole electron donor (1), 1.62 g/m² of N,N-diethyl-laurylamide, and 3.24 g/m² of gelatin; and (9) a protective layer containing 0.2 g/m² of tetrakis(vinylsulfonylmethine)methane and 0.90 g/m² of gelatin.

A processing sheet was subsequently prepared by coating on a 100 μm-thick transparent poly(ethylene terephthalate) film support in order from the support side the following layers:

(1) a neutralizing layer having 22 g/m² of an acrylic acid-butyl acrylate copolymer (75:25% by weight);

(2) a timing layer (the lower layer of a two-layer composition) having 5 g/m² of cellulose diacetate (acetylation degree: 40%); and (3) a timing layer (the upper layer of the two-layer composition) having 1.1 g/m² of a poly(vinylidene chloride-co-acrylonitrile-co-acrylic acid) (79:15:6% by weight).

The above-prepared multilayered, multicolor photographic element was subjected to a given exposure through an optical 30-step silver wedge with its each step density differential of 0.15, and after that the above-prepared processing sheet was superposed on the exposed photographic element, and further a pod containing about 1.0 ml of a processing composition having the following components was attached to between said superposed sheets, whereby a film unit was prepared. The pod was subsequently ruptured by passing the resulting film unit between a pair of juxtaposed pressure rollers with the gap therebetween of 340 μm to thereby spread the content thereof between the photographic element and the processing sheet.

The components of the processing composition used herein are as follows:

| Processing composition | |
|---|---|
| Potassium hydroxide | 56.0 g |
| Sodium sulfide | 2.0 g |
| 4-hydroxymethyl-4-methyl-1-phenyl-pyrazolidone | 80.0 g |
| 5-methyl benzotriazole | 2.8 g |
| Carbon black (Reveu-450) | 150.0 g |
| (manufactured by Columbia Carbon) | 150.0 g |
| Carboxymethyl cellulose sodium salt (high viscosity, manufactured by Tokyo Kasei) | 50.0 g |
| Benzyl alcohol | 1.5 ml |
| Distilled water to make | 1000.0 ml |

Fifteen minutes later, the processed sheet was measured with respect to the densities thereof against blue, green and red lights. The results are shown in Table 1.

TABLE 1

| | (measured results: reflection densities) | | |
|---|---|---|---|
| | Light used in measurement | | |
| Exposure | Red light | Green light | Blue light |
| Exposed area | 0.20 | 0.25 | 0.27 |
| Unexposed area | 1.85 | 1.80 | 1.95 |

The structures of the BEND compounds used in the above example are as follows:

a. Cyan BEND compound (A)

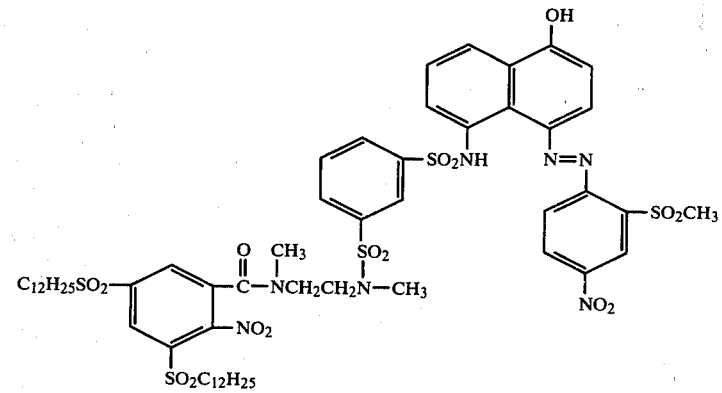

b. Magenta BEND compound (B)

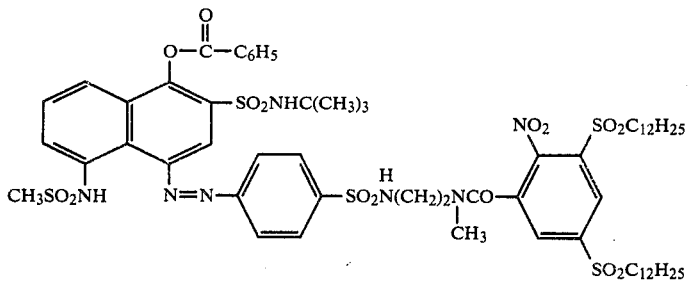

c. Yellow BEND compound (C)

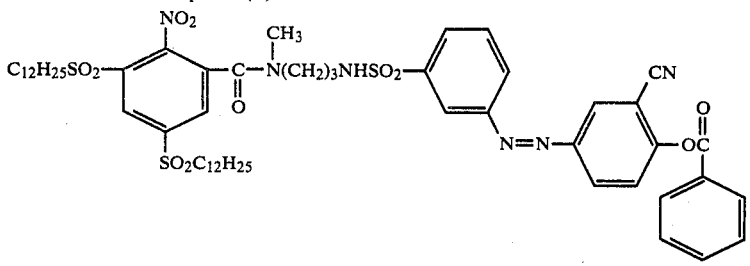

As apparent from Table 1, the use of the photographic element of the present invention enabled to obtain a high density-having diffusion dye positive image. In addition, the photographic element of the present invention showed that it is excellent in the stability thereof in the storage.

EXAMPLE 2

A multicolor image transfer type photographic element was prepared by coating on a 150 μm-thick transparent poly(ethylene terephthalate) film support in order from the support side the following layers:

(1) an image-receiving layer having 2.7 g/m² of gelatin and 2.7 g/m² of poly(styrene-co-N-benzyl-N,N-dimethyl-N-methacryloyl-aminophenyl-methyl ammonium chloride-co-divinyl benzene) (molar ratio: 48:48:4);

(2) a light-reflective-layer having 2.2 g/m² of gelatin and 22 g/m² of titanium dioxide;

(3) an opaque layer having 1.8 g/m² of gelatin and 2.8 g/m² of carbon black;

(4) a cyan dye-providing layer having 0.35 g/m² of the following cyan CLER compound (D), 0.20 g/m² of Exemplified pyrazole electron donor (3), 0.55 g/m² of N,N-diethyllaurylamide, and 1.65 g/m² of gelatin;

(5) a red-sensitive emulsion layer having 0.53 g Ag/m² of a red-sensitive silver iodobromide emulsion and 0.90 g/m² of gelatin;

(6) an interlayer having 0.45 g/m² of 2-acetyl-5-sec-octadecyl hydroquinone, 0.225 g/m² of dibutyl phthalate, and 1.0 g/m² of gelatin;

(7) a magenta dye-providing layer having 0.45 g/m² of the following magenta CLER compound (E), 0.29 g/m² of Exemplified pyrazole electron donor (3), 0.74 g/m² of N,N-diethyllaurylamide, and 2.22 g/m² of gelatin;

(8) a green-sensitive emulsion layer having 0.76 g Ag/m² of a green-sensitive silver iodobromide emulsion and 1.15 g/m² of gelatin;

(9) an interlayer having 0.45 g/m² of 2-acetyl-5-sec-octadecyl hydroquinone, 0.225 g/m² of dibutyl phthalate and 0.10 g/m² of gelatin;

(10) a yellow dye-providing layer having 0.50 g/m² of the following yellow CLER compound (F), 0.37 g/m² of Exemplified pyrazole electron donor (3), 0.87 g/m² of N,N-diethyllaurylamide, and 2.61 g/m² of gelatin;

(11) a blue-sensitive emulsion layer having 0.97 g Ag/m² of a blue-sensitive silver iodobromide emulsion and 1.50 g/m² of gelatin; and

(12) a protective layer having 0.2 g/m² of tetrakis(vinylsulfonyl methine) methane and 0.9 g/m² of gelatin.

The thus prepared multilayered, multicolor photographic element was subjected to a given exposure through an optical silver wedge, and then was superposed on the processing sheet prepared in Example 1, and further a pod containing the same processing composition as that used in Example 1 was attached to between the superposed sheets, thus preparing a film unit. The pod was then ruptured by passing the resulting film unit between a pair of juxtaposed pressure rollers to thereby spread the content thereof between the photographic element and the processing sheet. Fifteen minutes later, the processed sheet was measured with respect to the densities thereof to red, green and blue lights. The results obtained are shown in Table 2.

TABLE 2

| | (measured results: reflection densities) | | |
| --- | --- | --- | --- |
| | Lights used in measurement | | |
| Exposure | Red light | Green light | Blue light |
| Exposed area | 0.21 | 0.28 | 0.30 |
| Unexposed area | 1.78 | 1.73 | 1.90 |

The structures of the CLER compounds used in the above example are as follows:

a. Cyan CLER compound (D)

-continued

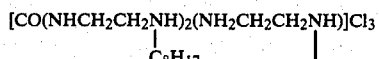
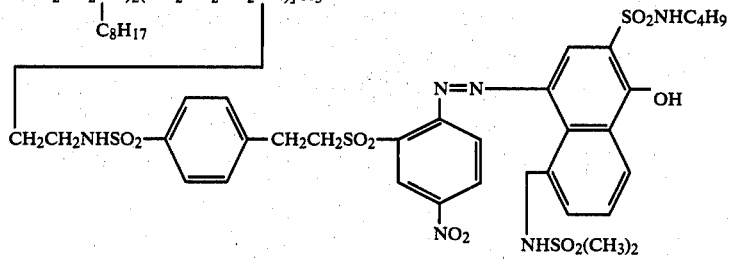

b. Magenta CLER compound (E)

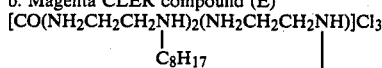
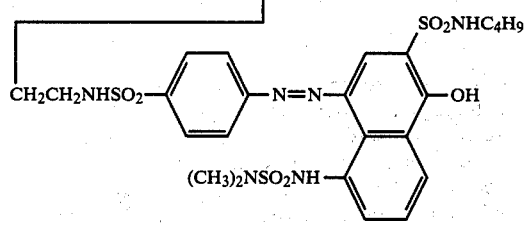

c. Yellow CLER compound (F)

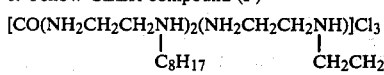
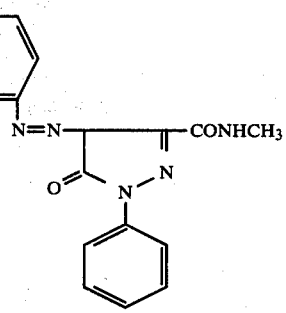

As apparent from the results shown in Table 2, the use of the photographic element of the present invention enabled to obtain a high density-having diffusion dye positive image. And the photographic element of the present invention showed that it is excellent in the stability and in the storage.

EXAMPLE 3

Two different photographic elements were prepared by the use of a pyrazole electron donor compound of the present invention and a known benz-iso-oxazole electron donor compound, respectively.

Sample of the present invention

A photographic element of the present invention was prepared by coating on a 150 μm-thick transparent poly(ethylene terephthalate) film support in order from the support side the following layers:

(1) an image-receiving layer having 2.7 g/m² of gelatin and 2.7 g/m² of poly(styrene-co-N-benzyl-N,N-dimethyl-N-methacryloyl-aminophenyl-methyl ammonium chloride-co-divinyl benzene) (molar ratio: 48:48:4);

(2) a white light-reflective layer having 2.2 g/m² of gelatin and 22 g/m² of titanium dioxide;

(3) an opaque layer having 1.8 g/m² of gelatin and 2.8 g/m² of carbon black;

(4) a green-sensitive, magenta dye-providing layer having 1.62 g Ag/m² of a green-sensitive silver iodobromide emulsion, 0.67 g/m² of the magenta BEND compound (B) described in Example 1, 0.96 g/m² of Exemplified pyrazole electron donor (3), 1.63 g/m² of N,N-diethyl-laurylamide, and 3.26 g/m² of gelatin; and (5) a protective layer composed of 0.2 g/m² of tetrakis(-vinylsulfonyl methine)methane and 0.90 g/m² of gelatin.

Control sample

A photographic element was prepared in the same manner as in the above with the exception that 1.22 g/m² of the following benz-iso-oxazole electron donor (G) was used in place of the 0.96 g/m² of the Exemplified pyrazole electron donor (3) in the layer (4).

Each of the above-prepared multilayered monochromatic photographic elements was subjected to a given exposure through an optical silver wedge, and was then superposed on the processing sheet prepared in Example 1, and further a pod containing the same processing composition as that used in Example 1 was attached to between the superposed sheets, thereby preparing a film unit. The pod was ruptured by passing the film unit between a pair of juxtaposed pressure rollers to thereby spread the content thereof between the photographic element and the processing sheet.

The change in the density of the processed sheet to a green light from immediately after to 30 minutes after the processing was sequentially measured, and the results of the measurement were obtained as shown in Table 3.

TABLE 3

|  | D (30 min) | T (0.5) | T (0.8) |
|---|---|---|---|
| Sample of the present invention | 1.83 | 1'10" | 3'50" |
| Control Sample | 1.71 | 1'30" | 4'20" |

Wherein D (30 min) represents Dmax density 30 minutes after the processing; T (0.5) represents the time required for the density to reach 50% of the density of D (30 min); and T (0.8) represents the time required for the density to reach 80% of the density of D (30 min).

The pyrazole electron donors of the present invention are so excellent that they have high Dmax densities and high image forming rates as compared to known benzoxazole electron donors.

The benzoxazole electron donor compound (G) has the formula:

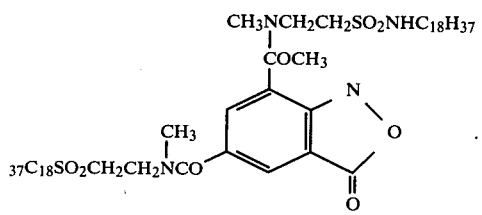

We claim:

1. A photographic element comprising a support provided thereon with at least one light-sensitive silver halide emulsion layer containing a nondiffusible compound which receives at least one electron in an alkaline condition to release a photographically useful material and a nondiffusible electron donor or a precursor thereof having the following formula (I) or (II):

Formula (I)     Formula (II)

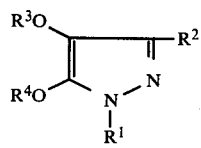   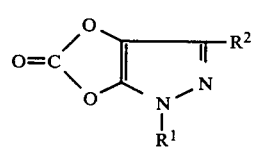

wherein $R^1$ represents hydrogen, an alkyl, an aryl or a heterocyclic group, $R^2$ represents hydrogen, an alkyl, an aryl, a heterocyclic, an amino, a carbamide, a sulfonamide, a sulfamoyl, a carbamoyl or a ureido group, $R^3$ and $R^4$ each is hydrogen, $-COR^5$, $-SO_2R^6$ or $-CSR^7$ wherein $R^5$ and $R^6$ each is a substituted or unsubstituted, respectively, alkyl, alkenyl, aryl, heterocyclic, alkylamino, arylamino, alkyloxy, aryloxy, alkylthio, arylthio, alkyloxycarbonyl or aryloxycarbonyl group, and $R^7$ is a substituted or unsubstituted alkylamino or arylamino group, said $R^4$ being allowed to form a ring together with said $R^1$.

* * * * *